United States Patent [19]

Slaugh

[11] 4,206,150
[45] Jun. 3, 1980

[54] AMINE PROCESS USING COPPER-MOLYBDENUM/TUNGSTEN CATALYST

[75] Inventor: Lynn H. Slaugh, Houston, Tex.

[73] Assignee: Shell Oil Company, Houston, Tex.

[21] Appl. No.: 968,245

[22] Filed: Dec. 11, 1978

Related U.S. Application Data

[63] Continuation-in-part of Ser. No. 956,298, Oct. 30, 1978, abandoned, which is a continuation of Ser. No. 738,491, Nov. 4, 1976, abandoned.

[51] Int. Cl.$^2$ .................. C07C 85/06; C07C 85/08
[52] U.S. Cl. ..................... 260/583 R; 260/563 R; 260/563 C; 260/570.8 R; 260/570.9; 260/583 P; 260/585 B; 260/585 C; 252/465; 252/467
[58] Field of Search ........... 260/583 R, 585 B, 585 C; 252/465, 467

[56] References Cited

U.S. PATENT DOCUMENTS

| | | | |
|---|---|---|---|
| 2,113,241 | 4/1938 | Punnett et al. | 260/585 B X |
| 2,285,419 | 6/1942 | Dickey et al. | 260/585 B X |
| 2,642,463 | 6/1953 | Arnold et al. | 260/585 C X |
| 3,520,933 | 7/1970 | Adam et al. | 260/585 B |

FOREIGN PATENT DOCUMENTS

| | | | |
|---|---|---|---|
| 48-85511 | 11/1973 | Japan | 260/585 |
| 49-81306 | 8/1974 | Japan | 260/585 |
| 436414 | 10/1935 | United Kingdom | 260/585 |

*Primary Examiner*—John E. Doll
*Attorney, Agent, or Firm*—Howard W. Haworth

[57] ABSTRACT

Amines are produced by reacting alcohols, aldehydes or ketones with ammonia, primary or secondary amines in the presence of a catalyst having improved selectivity and stability and which comprises a mixture of copper and molybdenum and/or tungsten supported on alumina.

9 Claims, No Drawings

AMINE PROCESS USING COPPER-MOLYBDENUM/TUNGSTEN CATALYST

This application is a continuation-in-part of application Ser. No. 956,298, filed Oct. 30, 1978, now abandoned which is a continuation of application Ser. No. 738,491, filed Nov. 4, 1976, now abandoned.

FIELD OF THE INVENTION

This invention is concerned with a process for making amines by reacting alcohols, aldehydes or ketones with ammonia, primary, or secondary amines in the presence of a catalyst comprising copper and molybdenum and/or tungsten supported on alumina.

SUMMARY OF THE INVENTION

This invention provides a process for producing amines by reacting alcohols, aldehydes or ketones with ammonia, primary or secondary amines in the presence of a specific catalyst. The catalyst contains a combination of metallic components: copper and molybdenum and/or tungsten, supported on an aluminum oxide carrier. This catalyst has the advantage of long life and high selectivity.

DESCRIPTION OF THE PREFERED EMBODIMENTS

The Catalyst

The catalyst of this invention is supported upon a suitable carrier. It comprises a mixture of components selected from the groups consisting of copper, copper oxide and mixtures thereof and molybdenum oxide, tungsten oxide and mixtures thereof with trioxides of molybdenum and tungsten being preferred. The weight percent of copper, either as copper or copper oxide or mixtures thereof (calculated on the basis of weight metal per total catalyst weight) ranges from about 0.005 to about 50, preferably from about 0.05 to about 40, and more preferably from about 0.1 to about 30. The weight percent of the molybdenum oxide, tungsten oxide or mixtures thereof (calculated on the basis of weight metal per total catalyst weight) ranges from about 0.005 to about 45, preferably from about 0.1 to about 35 and more preferably from about 0.15 to about 30.

The carriers suitable for the present process are conventional aluminum oxide carriers. Alumina carriers are readily available commercially. A preferred alumina carrier is gamma alumina.

The catalyst can be prepared in a number of suitable ways, as for example, by coprecipitation of the metal components on a powdered or pelleted carrier or by coprecipitation with the carrier from aqueous solution. A preferred method is to impregnate the carrier with solution of suitable salts of the active metals, and then to subsequently dry and calcine the impregnated carrier at temperatures ranging from about 100° C. to about 600° C. A preferred solvent is water, but certain organic solvents would also be suitable. Salts of the active metals soluble in the solvent are readily determined from common reference books. Useful salts for aqueous systems are chlorides, bromides, nitrates, acetates, lactates and the like. Ammonium salts are quite useful. Alternatively, solutions of salts of active metal and carrier could be spray dried and calcined at temperatures from about 100° C. to about 600° C.

The catalysts used in this invention are activated before use by heating in a reducing atmosphere, for example, in hydrogen or ammonia. The preferred atmosphere is hydrogen. Activation temperatures range from about 250° C. to about 600° C. The time needed for activation will depend on the temperature, the higher the temperature, the shorter the time. Typically, useful times have been found to range from about 0.1 hour to about 24 hours, although times outside these limits are also useful, economic considerations, however, tending to dictate against their use.

The Process

Preferred reactant hydrocarbon materials are aliphatic, cycloaliphatic, araliphatic or aromatic alcohols, ketones or aldehydes having up to twenty-five, preferably up to twenty carbon atoms. These starting materials may be unsaturated, containing for example one or two olefinic double bonds. They also may contain substituents which are inert under the reaction conditions, such as alkyl groups having one to four carbon atoms which are attached via either bridges. Particulur industrial importances attaches to aliphatic or cycloaliphatic alcohols having up to twenty carbon atoms. Examples of suitable alcohols/aldehydes are ethanol/al, propanol/al, isopropanol, butanol/al, isobutanol/al, 2-ethylhexanol/al, decanol/al, dodecanol/al, hexadecanol/al, cyclopentol, cyclohexanol, cyclooctanolcyclododecanol, benzyl alcohol/aldehyde, phenylethyl alcohol/aldehyde, 1,4-butanediol/al, 1,6-hexanediol/al, 1,5-pentadiol/al, 1,8-octanediol/al and the like. Examples of suitable ketones are acetone, methylethyl ketone, methylisobutyl ketone, phenylmethyl ketone, phenylethyl ketone, 3-decanone, 5-dodecanone cyclopentanone, cyclohexanone, cyclooctanone, cyclododecanone and the like.

Preferred reactant amine materials are primary or secondary amines. Alkylamines, cycloalkylamines, or aralkylamines having one to twelve carbon atoms, particularly alkylamines having one to four carbon atoms and one amine group in the molecule are preferred. Examples of suitable amines are monomethylamine, dimethylamine, methylethylamine, monoethylamine, diethylamine, and the like. Preferred reactant amines are monomethylamine and dimethylamine.

The reactant alcohols, aldehydes or ketones are advantageously reacted with at least an equivalent amount of ammonia or reactant amines and are also advantageously used in excess, for example, up to 50 preferably up to 20 moles of ammonia or reactant amine per reactant hydroxyl or carbonyl group. The ratio of ammonia or reactant amine to reactant alcohol preferably ranges from about 1:1 to about 50:1.

The reaction is advantageously carried at temperatures of from about 60° C. to about 350° C. Preferred temperatures range from about 180° C. to about 300° C. Reaction pressures range from about 15 psi to about 4000 psi, and preferably from about 150 psi to about 1000 psi. It is preferred to carry out the reaction in the presence of hydrogen. It is advantageous to use partial pressures of hydrogen of from about 10 psi to about 3000 psi, preferably from about 100 psi to about 1000 psi. It is advantageous to use a hydrogen to alcohol, aldehyde or ketone molar ratio greater than one. The reaction system may also be partially pressurized with inert gases such as nitrogen, argon.

The reaction may be conducted batchwise or in a continuous operation. By way of illustration of the batchwise process, a highpressure, stirred autoclave is charged with alcohol, aldehyde, or ketone, reactant amine, or ammonia and catalyst, pressurized with hydrogen, and heated to reaction temperature. After the reaction is allowed to proceed for the desired length of time, the autoclave is cooled, the excess hydrogen vented, and the products worked up by conventional methods. By ways of illustration of continuous operation, a vertical, high-pressure column is charged with catalyst, and alcohol and reaction amine are supplied at the top. At the same time hydrogen is metered into the column in cocurrent or countercurrent flow. The hydrogen is advantageously recycled. During the reaction appropriate conditions of temperature and pressure are maintained. The reaction product is removed from the bottom of the column, freed from hydrogen and worked up by conventional methods. An alternate continuous process entails allowing the reaction mixture in which the catalyst is dispersed to trickle over fillers or baffles in a tower.

The process of this invention is further described by the following illustrative embodiments which are provided for illustration and are not to be construed as limiting the invention.

Illustrative Embodiment I: The Catalyst

Part A: Copper/Tungsten Catalyst

A fifteen ml deionized water solution containing 9.6 g of copper nitrate was combined with a water solution containing 3 g of ammonium metatungstate. Without delay, the resultant solution was added with good mixing to 48 g of 18×30 mesh Reynolds RA-1 alumina (surface area of about 260 $m^2$/gm and pore volume of about 0.26 cc/gm). The catalyst was stirred gently for 15 minutes while being dried with warm air. The catalyst was then placed in a vycor tube and heated in a stream of air (500 ml/min) from 25° C. to 500° C. in 50° increments. The time of heating was 30 minutes at 100° C. and 15 minutes at 50° temperature increment thereafter. The resultant cooled, calcined catalyst was subsequently reduced with hydrogen diluted with nitrogen as the temperature was gradually increased to 500° C.

Part B: Copper/Molybdenum Catalyst 9.6 G of copper nitrate were heated with 40 ml of aqueous ammonium hydroxide (28–30% $NH_3$) to make a solution. 2 G of ammonium molybdate were dissolved in the above solution and about one-half this resultant solution was used to impregnate 48 g of 18×30 mesh Reynolds RA-1 alumina. The impregnated carrier was dried in air in 50° C. stages from 100° C. to 300° C., cooled down and impregnated with the remaining solution. The drying process was repeated, but this time continuing up to 500° C. The catalysts were then reduced in hydrogen at a temperature up to 500° C.

Illustrative Embodiment II: The Process

1. A copper/tungsten on alumina catalyst was prepared similar to the method described in Illustrative Embodiment I, part A above and contained 3.3%w Cu and 3.9%w W. The catalyst (10 cc) was charged to the trickle phase reactor and dimethylamine and n-butanol were fed to the reactor at a LHSV of about 1 and a molar ratio of amine to alcohol of 3:1. Hydrogen was metered into the reactor at a rate of 100 cc/min. and a pressure of 375 psi was maintained. The reactor temperature was about 214° C. After a run time of 4 hours, an analysis of the product showed an 89.3 mol % conversion of the alcohol, a selectivity of 80.9 mol % to dimethylbutylamine, a selectivity of 10.8 mol % to methyl-butylamine and a selectivity to $C_8$ and $C_9$ amines of 8.3 mol %.

2. A copper/tungsten on alumina catalyst was prepared similar to the method described in Illustrative Embodiment I, part A above and contained 5.1%w Cu and 4.2%w W. The catalyst (10 cc) was charged to the trickle phase reactor and dimethylamine and lauraldehyde were fed to the reactor at a LHSV of about 1 and a molar ratio of amine to aldehyde of about 3:1. Hydrogen was metered into the reactor at a rate of 100 cc/min. Pressure was maintained at 375 psi. Temperature of the reactor was 183° C. After a run time of one hour an analysis of the product showed an 95.8 mol % conversion of aldehyde with an 80.7 mol % selectivity to dimethyldodecylamine, a 19.3 mol % selectivity to $C_{24}$ plus $C_{25}$ amines and a trace amount of methyldodecylamine. After a rum time of 2.75 hours, aldehyde conversion was 85.3 mol %, selectivity to dimethyldodecylamine was 76.8 mol %, selectivity to $C_{24}$ and $C_{25}$ amines was 23.2 mol % and trace amounts of methyldodecylamine was present.

3. A copper/molybdenum on alumina catalyst was prepared similar to the method given in Illustrative Embodiment I, part B above and contained 4.7%w Cu and 2.0%w Mo. The catalyst (10cc) was charged to the trickle phase reactor and dimethylamine and 1-dodecanol were fed to the reactor as a LHSV of about 1 and a molar ratio of amine to alcohol of 3:1. Hydrogen was metered into the reactor at a rate of 100 cc/min. Pressure was maintained at 375 psi. Temperature was maintained at 225° C. After a run time of one hour an analysis of the product showed a 93.3 mol % conversion of alcohol with a selectivity to dimethyldodecylamine of 82.6 mol %, a selectivity to methyldodecylamine of 8.2 % and a selectivity to $C_{24}$ plus $C_{25}$ amine of 9.2 mol %. After a run period of three hours, alcohol conversion was 73.5 mol %, selectivity to dimethyldodecylamine was 87.8 mol %, selectivity to methyldodecylamine was 6.1 mol % and selectivity to $C_{24}$ plus $C_{25}$ amines was 6.1 mol %.

4. A life test was performed on a copper/tungsten on alumina catalyst made according to this invention. The catalyst was prepared by a method similar to Part A, Illustrative Embodiment I, above. The catalyst product contained 3.3%w Cu and 3.9%w W. Twenty-five cubic centimeters of the catalyst was charged to a trickle phase reactor and monomethylamine and a Neodol 45 ® alcohol which comprises a mixture of 14 and 15 carbon number alcohols was fed to the reactor at a molar ratio of amine to Neodol alcohol of 3:1 and at a liquid hourly space velocity of 1. Hydrogen was metered into the reactor at a rate of 750 cc/min (STP) and a pressure of 400 psi was maintained. Results are shown in Table I. No evidence of leaching of copper (blue color) into the product was noted.

Table I:

| | | | Life Test of Copper/Tungsten Catalyst | | |
| --- | --- | --- | --- | --- | --- |
| | | | | Selectivity, mol % | |
| Run Time Hours | Temp. °C. | Alcohol Conv. mol % | Methyl-dodecyl-amine | Di-methyl-dodecyl-amine | $C_{24}$ plus $C_{25}$ amine |
| 2 | 199 | 93.7 | 87.8 | 2.7 | 9.4 |
| 3.6 | 208 | 93.1 | 82.1 | 3.1 | 14.9 |
| 19.6 | 208 | 91.0 | 75.2 | 5.2 | 19.6 |
| 27.9 | 208 | 87.4 | 79.4 | 4.1 | 16.5 |
| 44.3 | 208 | 79.3 | 82.2 | 3.2 | 14.6 |

5. A life test was performed on a copper/tungsten on alumina catalyst prepared as in the method described in Illustrative Embodiment part A above. The catalyst contained 3.6%w Cu and 3.9%w W. The catalyst (10 cc) was charged to the trickle phase reactor and dimethylamine and 1-dodecanol were fed to the reactor at a liquid hourly space velocity of 1 and a molar ratio of amine to alcohol of 3:1. Hydrogen was metered into the reactor at a rate of 100 cc/min and a pressure of 400 psi was maintained. The results are shown in Table II. No evidence of leaching of copper (blue color) into the product was noted.

Table II

Life Test of Copper/Tungsten Catalyst

| Run Time Hours | Temp. °C. | Alcohol Conv. mol % | Selectivity, mol % | | |
|---|---|---|---|---|---|
| | | | Dimethyldodecylamine | Methyldodecylamine | $C_{24}$ plus $C_{25}$ amine |
| 2.2 | 203 | 95.7 | 76.2 | 7.9 | 15.9 |
| 3.7 | 198 | 87.4 | 84.3 | 8.2 | 7.5 |
| 20.1 | 203 | 95.0 | 82.5 | 6.4 | 11.1 |
| 28.0 | 203 | 94.7 | 79.7 | 7.9 | 12.4 |
| 44.5 | 203 | 94.5 | 80.7 | 6.4 | 12.9 |
| 68.3 | 203 | 95.8 | 80.2 | 6.9 | 12.9 |
| 94.4 | 193 | 92.5 | 80.9 | 7.8 | 11.2 |
| 126.0 | 195 | 96.3 | 80.8 | 6.6 | 12.6 |

Comparative Experiments

6. A catalyst was prepared by impregnating an alumina support (RA-1) with a 50%w aqueous solution of copper nitrate and then reducing the impregnated support in hydrogen at 500° C. The catalyst contained 10%w copper. The catalyst (10 cc) was charged to a trickle phase reactor having a volume of about 25 cc and monomethylamine and 1-dodecanol were fed to the reactor at a liquid hourly space velocity (LHSV) of 1.1 and a molar ratio of amine of alcohol of 3. The reactor was maintained at a temperature of 200° C. Hydrogen was metered into the reactor at a rate of 100 cc per minute (STP) and pressure was maintained at 375 psi. After 5 hours of operation the conversion of dodecanol was 92.7 mol %, selectivity to methyldodecylamine was 85.9 mol % and selectivity to $C_{24}$ plus $C_{25}$ amines was 14.1 mol %. The above experiment was repeated and after 3 hours of operation, the alcohol conversion was 86.8%, selectivity to methyldodecylamine was 72.1% and selectivity to $C_{24}$ plus $C_{25}$ amines was 21.3%. Stability of the catalyst was poor as evidenced by leaching of copper (blue color) into product.

7. Ten cubic centimeters of a copper on alumina catalyst was prepared and tested as in part 1 above. The catalyst contained 3.9%w copper. The feed in this case was dimethylamine and 1-dodecanol in a molar ratio of 3:1. LHSV was 1.1 and the reactor temperature was maintained at about 220° C. Hydrogen was metered into the reactor at a rate of 100 cc per minute (STP) and pressure was maintained at 375 psi. After 2 hours of operation, the conversion of dodecanol was 80.6%, selectivity to dimethyldodecylamine was 72.2%, selectivity to methyldodecylamine was 20.4% and selectivity to $C_{25}$ amines was 7.4%. After three hours of operation conversion of alcohol was 81.7%, selectivity to dimethyldodecylamine was 69.7%, to methyldodecylamine was 20.1% and to $C_{25}$ amines was 10.2%. Stability of the catalyst was poor as evidenced by leaching of copper (blue color) into the product.

8. A tungsten on alumina catalyst (4.6%w) was prepared in a manner similar to Part A Illustrative Embodiment I above except that no copper was utilized. The catalyst (10 cc) was charged to the trickle phase reactor and dimethylamine and 1-dodecanol were fed to the reactor at a liquid hourly space velocity of 1.1 and a molar ratio of 3:1. Reactor temperature was about 225° C. and pressure was about 375 psi. Hydrogen was metered into the reactor at a rate of 100 cc/min. After 4 hours of operation, conversion was found to be only 3 mol %.

9. Catalysts using different supports were prepared by a method similar to Part A Illustrative Embodiment I above and were tested as above. The catalysts (10 cc) were individually charged to to trickle phase reactor and dimethylamine and 1-dodecanol were fed to the reactor at a LHSV of about 1 and molar ratio of amine to alcohols of 3:1. Hydrogen was metered into the reactor at a rate of 100 cc/min. pressure was maintained at 375 psi. The results are shown in Table III.

Table III

Effect of Supports

| Catalyst | Time Hours | Temp. °C. | Alcohol Conv. mol % |
|---|---|---|---|
| 4.8%w Cu/1.5%w Mo on Kielselguhr | 3 | 225 | 13.1 |
| 5.5w Cu/1.9%w Mo on silica-alumina | 4 | 225 | 22.4 |
| 3.1%w Cu/1.6%w Mo on silica | 5 | 225 | 70.7 |
| 5.6%w Cu/5.5%w on silica-alumina | 3 | 225 | 12.6 |
| 3.2%w Cu/1.1%w Mo on carbon | 2 | 250 | 63.6 |

| Selectivity, mol % | | |
|---|---|---|
| Methyldodecylamine | Dimethyldodecylamine | $C_{24}$ + $C_{25}$ amines |
| 14.8 | 74.4 | 10.8 |
| 21.1 | 72.2 | 6.8 |
| 4.8 | 84.9 | 5.5 |
| 15.6 | 79.8 | 4.7 |
| 16.4 | 57.0 | 26.6 |

10. A catalyst was prepared by impregnating an alumina support with a 55%w aqueous solution of nickel nitrate, and then reducing the impregated support in hydrogen at 500° C. The catalyst contained 10%w nickel. The catalyst (10 cc) was charged to a trickle phase reactor. Monomethylamine and 1-dodecanol were fed to the reactor at a liquid hourly space velocity of 1.1 and a molar ratio of amine to alcohol of 3. The reactor was maintained at a temperature of 190° C. Hydrogen at a flow rate of 100 cc/min was maintained at 275 psi. After 3 hours of operation, the conversion of deodecanol was 58.4, selectivity to methyldodcylamine was 30.9%, selectivity to dimethyldodecylamine was 16.8% and selectivity to $C_{24}$ and $C_{25}$ amines was 51.6%.

11. A catalyst was prepared by impregnation of an alumina support with an aqueous solution of copper nitrate and chromium nitrate. The impregnated support was calcined in air at 500° C. for 1.0 hour followed by reduction in 375 psi hydrogen up to 300° C. for 1.5 hours. The catalyst contained 5.5%w Cu and 1.2%w Cr. The catalyst (10 cc) was charged to a trickle phase reactor and monomethylamine and 1-dodecanol were fed to the reactor at a liquid hourly space velocity of 1.1 and a molar ratio of amine to alcohol of 3. The reactor was maintained at a temperature of 190° C. Hydrogen was metered into the reactor at a rate of 100 cc/min (STP) and pressure was maintained at 375 psi. After 3 hours of operation, the conversion of dodecanol was 88.2%, selectivity to methyldodecylamine was 76.6% and selectivity to $C_{24}$ plus $C_{25}$ amines was 20.3%.

12. A catalyst was prepared by impregnation of alumina with an aqueous solution of copper nitrate and zinc nitrate. The impregnated support was calcined at 500° C. The catalyst contained 5%w Cu and 3%w Zn. The catalyst (10 cc) was charged to a trickle phase reactor and monomethylamine and 1-dodecanol were fed to the reactor at a liquid hourly space velocity of 1.1 and a molar ratio of amine to alcohol of 2. The reactor temperature was 192° C. Reactor pressure was 375° psi, maintained by hydrogen flowing at a rate of 100 cc/min. After 4 hours of operation, the conversion of dodecanol was 83.3%, selectivity to methyldodecylamine was 65.9% and selectivity to $C_{24}$ plus $C_{25}$ amines was 31.4%.

13. A life test was performed on a Cu/Zn catalyst made not according to this invention. The catalyst was prepared by impregnating Reynolds RA-1 aluminum with a solution containing copper nitrate and zinc nitrate. The material was then calcined and reduced with hydrogen at 500° C. The catalyst contained 4.9%w Cu and 3%w Zn. The catalyst (10 cc) was charged to a trickle phase reactor and monomethylamine and 1-dodecanol were fed to the reactor at a liquid hourly space velocity of 1, and a molar ratio of amine to alcohol of 3:1. Hydrogen was metered into the reactor at a rate of 100 cc/mm and pressure was maintained at 420 psi. Results are shown in Table IV.

Table IV:

| | Life Tests of Cu/Zn Catalyst | | | |
|---|---|---|---|---|
| Time of | | | Selectivity, mol% | |
| Run, Hours | Temp. °C. | Alcohol Conv., Mol % | Methyldo- decylamine | $C_{24}$ plus $C_{25}$ amines |
| 22.5 | 200 | 89.9 | 83.9 | 13.6 |
| 46.7 | 205 | 94.1 | 70.8 | 24.3 |
| 51.7 | 205 | 91.2 | 67.8 | 28.0 |
| 70.3 | 205 | 95.3 | 68.7 | 26.6 |
| 73.0 | 205 | 95.3 | 71.7 | 24.1 |

14. A life test was performed on a Cu/Cr catalyst made not according to this invention. Results are shown in Table V below.

Table V

| | Life of Cu/Cr Catalyst | | | |
|---|---|---|---|---|
| Time | | | Selectivity, mol% | |
| of Run, Hours | Temp. °C. | Alcohol Conv., Mol % | Methyldo- decylamine | $C_{24}$ plus $C_{25}$ amines |
| 25 | 206 | 95.7 | 78.7 | 17.4 |

The product was contaminated with metals which had been leached from the catalyst during use.

What is claimed is:

1. A process for preparing amines which comprises reacting alcohols, aldehydes or ketones having up to twentty-five carbon atoms with ammonia or primary or secondary amines having one to eight carbon atoms in a reducing atmosphere in the presence of a supported alumina catalyst comprising a mixture of a first component selected from the group consisting of copper, copper oxide and mixtures thereof with the copper, measured as the metal, ranging from about 0.005 to about 50 weight percent of the total catalyst and a second component selected from the group consisting of an oxide of molybdenum, tungsten and mixtures thereof with the second component, measured as the metal, ranging from about 0.005 to about 45 weight percent of the total catalyst.

2. The process of claim 1 wherein the first component ranges from about 0.05 percent weight to about 40 percent weight and the second component ranges from about 0.1 percent weight to about 35 percent weight.

3. The process of claim 1 wherein the reducing atmosphere is hydrogen.

4. The process of claim 3 wherein the hydrogen is maintained at a partial pressure from about 15 to about 4000 psi.

5. The process of claim 1 wherein the reaction is carried out at a temperature of from about 160° C. to about 350° C.

6. The process of claim 1 wherein an alcohol is reacted with monomethylamine.

7. The process of claim 6 wherein the ratio of monomethylamine to alcohol ranges from about 1:1 to about 50:1.

8. The process of claim 1 wherein an alcohol is reacted with dimethylamine.

9. The process of claim 8 wherein the ratio of dimethylamine to alcohol ranges from about 1:1 to about 50:1.

* * * * *